(12) United States Patent
Benichou et al.

(10) Patent No.: US 6,358,751 B1
(45) Date of Patent: Mar. 19, 2002

(54) INVOLVEMENT OF AUTOANTIGENS IN CARDIAC GRAFT REJECTION

(75) Inventors: Gilles Benichou; Eugenia Fedoseyeva, both of West Newton, MA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/310,187

(22) Filed: May 12, 1999

(51) Int. Cl.$^7$ .............................................. G01N 33/564
(52) U.S. Cl. ........................... 436/506; 436/507; 435/4; 435/7.1; 435/29
(58) Field of Search ............................. 435/4, 7.1, 29; 436/506, 507

(56) References Cited

PUBLICATIONS

Barany, (1985) *Gene*, vol. 37:111–123.
Benichou, et al., (1994) *International Immunology*, vol. 6, No. (1):131–138.
Benichou, et al., (1990) *J. Exp. Med.*, vol. 172:1341–1346.
Benichou, et al., (1999) *Journal of Immunology*, vol. 162:352–358.
Colicelli, et al., (1985) *Mol. Gen. Genet.*, vol. 199:537–539.
Corry, et al., (1973) *Transplantation*, vol. 16, No. (4):343–350.
Even, et al., (1995) *Res. Immunol.*, vol. 146:65–80.
Gustin, et al. (1993) *BioTechniques*, vol. 14, No. (1):22.
Jewell, et al., (1998) *Immunology and Cell Biology*, vol. 76:74–82.
Kaufman, et al., (1993) *Nature*, vol. 366:69–72.
Kurabayashi, et al., (1988) *J. Clin. Invest.*, vol. 82:524–531.
Liblau, et al., (1995) *Immunology Today*, vol. 16, No. (1):34–38.
Metzler, et al., (1993) *International Immunology*, vol. 5, No. (9):1159–1165.
Mosmann, et al., (1989) *Ann. Rev. Immunol.*, vol. 7:145–173.
Neu, et al., (1987) *Journal of Immunology*, vol. 138, No. (8):2488–2492.
Pannetier, et al., (1995) *Immunology Today*, vol. 16, No. (4):176–181.
Prentki, et al., (1984) *Gene*, vol. 29:303–313.
Rabinovitch, (1994) *Diabetes*, vol. 43:613–621.
Shiverick, et al., (1975) *Biochimica et Biophysica Acta*, vol. 393:124–133.
Schütz, et al., (1997) *Ann. Thorac. Surg.*, vol. 63:578–581.
Tian, et al., (1996) *Nature Medicine*, vol. 2, No. (12):1348–1353.
Tisch, et al., (1994) *Proc. Natl. Acad. Sci. U.S.A.*, vol. 91:437–438.
Trentham, et al., (1993) *Science*, vol. 261:1727–1730.
Zhang, et al., (1995) *The Journal of Immunology*, vol. 155:5868–5877.

*Primary Examiner*—Patrick J. Nolan
(74) *Attorney, Agent, or Firm*—Pamela J. Sherwood; Boziecevic, Field & Francis LLP

(57) ABSTRACT

Allograft rejection is initiated by an immune response to donor major histocompatibility complex proteins. After allogeneic heart transplantation, de novo CD4+ T cell and B cell autoimmune responses to contractile proteins of cardiac muscle, e.g. cardiac myosin (CM), are elicited. The transplantation induced autoimmune response to cardiac myosin plays an significant role in cardiac transplant rejection. Methods are provided for diagnosis and therapy of graft rejection.

12 Claims, 5 Drawing Sheets

SEQUENCE LISTING

<160> NUMBER OF SEQ ID NOS: 3

<210> SEQ ID NO 1
<211> LENGTH: 1939
<212> TYPE: PRT
<213> ORGANISM: Homo sapiens

<400> SEQUENCE: 1

```
Met Thr Asp Ala Gln Met Ala Asp Phe Gly Ala Ala Gln Tyr Leu
 1               5                  10                  15

Arg Lys Ser Glu Lys Glu Arg Leu Glu Ala Gln Thr Arg Pro Phe Asp
                20                  25                  30

Ile Arg Thr Glu Cys Phe Val Pro Asp Asp Lys Glu Phe Val Lys
                35                  40                  45

Ala Lys Ile Leu Ser Arg Glu Gly Lys Val Ile Ala Glu Thr Glu
 50                  55                  60

Asn Gly Lys Thr Val Thr Val Lys Glu Asp Gln Val Leu Gln Gln Asn
 65                  70                  75                  80

Pro Pro Lys Phe Asp Lys Ile Gln Asp Met Ala Met Leu Thr Phe Leu
                85                  90                  95

His Glu Pro Ala Val Leu Phe Asn Leu Lys Glu Arg Tyr Ala Ala Trp
                100                 105                 110

Met Ile Tyr Thr Tyr Ser Gly Leu Phe Cys Val Thr Val Asn Pro Tyr
                115                 120                 125

Lys Trp Leu Pro Val Tyr Asn Ala Glu Val Val Ala Ala Tyr Arg Gly
                130                 135                 140

Lys Lys Arg Ser Glu Ala Pro Pro His Ile Phe Ser Ile Ser Asp Asn
145                 150                 155                 160

Ala Tyr Gln Tyr Met Leu Thr Asp Arg Glu Asn Gln Ser Ile Leu Ile
                165                 170                 175

Thr Gly Glu Ser Gly Ala Gly Lys Thr Val Asn Thr Lys Arg Val Ile
                180                 185                 190

Gln Tyr Phe Ala Ser Ile Ala Ala Ile Gly Asp Arg Gly Lys Lys Asp
                195                 200                 205

Asn Ala Asn Ala Asn Lys Gly Thr Leu Glu Asp Gln Ile Ile Gln Ala
        210                 215                 220

Asn Pro Ala Leu Glu Ala Phe Gly Asn Ala Lys Thr Val Arg Asn Asp
225                 230                 235                 240

Asn Ser Ser Arg Phe Gly Lys Phe Ile Arg Ile His Phe Gly Ala Thr
                245                 250                 255

Gly Lys Leu Ala Ser Ala Asp Ile Glu Thr Tyr Leu Leu Glu Lys Ser
                260                 265                 270

Arg Val Ile Phe Gln Leu Lys Ala Glu Arg Asn Tyr His Ile Phe Tyr
                275                 280                 285

Gln Ile Leu Ser Asn Lys Lys Pro Glu Leu Leu Asp Met Leu Leu Val
                290                 295                 300

Thr Asn Asn Pro Tyr Asp Tyr Ala Phe Val Ser Gln Gly Glu Val Ser
305                 310                 315                 320

Val Ala Ser Ile Asp Asp Ser Glu Glu Leu Met Ala Thr Asp Ser Ala
                325                 330                 335

Phe Asp Val Leu Gly Phe Thr Ser Glu Glu Lys Ala Gly Val Tyr Lys
                340                 345                 350

Leu Thr Gly Ala Ile Met His Tyr Gly Asn Met Lys Phe Lys Gln Lys
```

```
            355                 360                 365
Gln Arg Glu Glu Gln Ala Glu Pro Asp Gly Thr Glu Asp Ala Asp Lys
        370                 375                 380

Ser Ala Tyr Leu Met Gly Leu Asn Ser Ala Asp Leu Leu Lys Gly Leu
385                 390                 395                 400

Cys His Pro Arg Val Lys Val Gly Asn Glu Tyr Val Thr Lys Gly Gln
                405                 410                 415

Ser Val Gln Gln Val Tyr Tyr Ser Ile Gly Ala Leu Ala Lys Ala Val
                420                 425                 430

Tyr Glu Lys Met Phe Asn Trp Met Val Thr Arg Ile Asn Ala Thr Leu
            435                 440                 445

Glu Thr Lys Gln Pro Arg Gln Tyr Phe Ile Gly Val Leu Asp Ile Ala
        450                 455                 460

Gly Phe Glu Ile Phe Asp Phe Asn Ser Phe Glu Gln Leu Cys Ile Asn
465                 470                 475                 480

Phe Thr Asn Glu Lys Leu Gln Gln Phe Phe Asn His His Met Phe Val
                485                 490                 495

Leu Glu Gln Glu Glu Tyr Lys Lys Glu Gly Ile Glu Trp Thr Phe Ile
            500                 505                 510

Asp Phe Gly Met Asp Leu Gln Ala Cys Ile Asp Leu Ile Glu Lys Pro
        515                 520                 525

Met Gly Ile Met Ser Ile Leu Glu Glu Glu Cys Met Phe Pro Lys Ala
        530                 535                 540

Thr Asp Met Thr Phe Lys Ala Lys Leu Tyr Asp Asn His Leu Gly Lys
545                 550                 555                 560

Ser Asn Asn Phe Gln Lys Pro Arg Asn Ile Lys Gly Lys Gln Glu Ala
                565                 570                 575

His Phe Ser Leu Ile His Tyr Ala Gly Thr Val Asp Tyr Asn Ile Leu
            580                 585                 590

Gly Trp Leu Glu Lys Asn Lys Asp Pro Leu Asn Glu Thr Val Val Ala
            595                 600                 605

Leu Tyr Gln Lys Ser Ser Leu Lys Leu Met Ala Thr Leu Phe Ser Ser
        610                 615                 620

Tyr Ala Thr Ala Asp Thr Gly Asp Ser Gly Lys Ser Lys Gly Gly Lys
625                 630                 635                 640

Lys Lys Gly Ser Ser Phe Gln Thr Val Ser Ala Leu His Arg Glu Asn
                645                 650                 655

Leu Asn Lys Leu Met Thr Asn Leu Arg Thr Thr His Pro His Phe Val
            660                 665                 670

Arg Cys Ile Ile Pro Asn Glu Arg Lys Ala Pro Gly Val Met Asp Asn
        675                 680                 685

Pro Leu Val Met His Gln Leu Arg Cys Asn Gly Val Leu Glu Gly Ile
        690                 695                 700

Arg Ile Cys Arg Lys Gly Phe Pro Asn Arg Ile Leu Tyr Gly Asp Phe
705                 710                 715                 720

Arg Gln Arg Tyr Arg Ile Leu Asn Pro Val Ala Ile Pro Glu Gly Gln
                725                 730                 735

Phe Ile Asp Ser Arg Lys Gly Thr Glu Lys Leu Leu Ser Ser Leu Asp
            740                 745                 750

Ile Asp His Asn Gln Tyr Lys Phe Gly His Thr Lys Val Phe Phe Lys
            755                 760                 765

Ala Gly Leu Leu Gly Leu Leu Glu Glu Met Arg Asp Glu Arg Leu Ser
        770                 775                 780
```

-continued

```
Arg Ile Ile Thr Arg Met Gln Ala Gln Ala Arg Gly Gln Leu Met Arg
785                 790                 795                 800

Ile Glu Phe Lys Lys Ile Val Glu Arg Arg Asp Ala Leu Leu Val Ile
                805                 810                 815

Gln Trp Asn Ile Arg Ala Phe Met Gly Val Lys Asn Trp Pro Trp Met
            820                 825                 830

Lys Leu Tyr Phe Lys Ile Lys Pro Leu Leu Lys Ser Ala Glu Thr Glu
            835                 840                 845

Lys Glu Met Ala Thr Met Lys Glu Glu Phe Gly Arg Ile Lys Glu Thr
        850                 855                 860

Leu Glu Lys Ser Glu Ala Arg Arg Lys Glu Leu Glu Glu Lys Met Val
865                 870                 875                 880

Ser Leu Leu Gln Glu Lys Asn Asp Leu Gln Leu Gln Val Gln Ala Glu
                885                 890                 895

Gln Asp Asn Leu Asn Asp Ala Glu Glu Arg Cys Asp Gln Leu Ile Lys
            900                 905                 910

Asn Lys Ile Gln Leu Glu Ala Lys Val Lys Glu Met Asn Glu Arg Leu
        915                 920                 925

Glu Asp Glu Glu Glu Met Asn Ala Glu Leu Thr Ala Lys Lys Arg Lys
930                 935                 940

Leu Glu Asp Glu Cys Ser Glu Leu Lys Lys Asp Ile Asp Asp Leu Glu
945                 950                 955                 960

Leu Thr Leu Ala Lys Val Glu Lys Glu Lys His Ala Thr Glu Asn Lys
                965                 970                 975

Val Lys Asn Leu Thr Glu Glu Met Ala Gly Leu Asp Glu Ile Ile Ala
            980                 985                 990

Lys Leu Thr Lys Glu Lys Lys Ala Leu Gln Glu Ala His Gln Gln Ala
        995                 1000                1005

Leu Asp Asp Leu Gln Val Glu Glu Asp Lys Val Asn Ser Leu Ser Lys
        1010                1015                1020

Ser Lys Val Lys Leu Glu Gln Gln Val Asp Asp Leu Glu Gly Ser Leu
1025                1030                1035                1040

Glu Gln Glu Lys Lys Val Arg Met Asp Leu Glu Arg Ala Lys Arg Lys
                1045                1050                1055

Leu Glu Gly Asp Leu Lys Leu Thr Gln Glu Ser Ile Met Asp Leu Glu
            1060                1065                1070

Asn Asp Lys Leu Gln Leu Glu Glu Lys Leu Lys Lys Lys Glu Phe Asp
            1075                1080                1085

Ile Asn Gln Gln Asn Ser Lys Ile Glu Asp Glu Gln Ala Leu Ala Leu
        1090                1095                1100

Gln Leu Gln Lys Lys Leu Lys Glu Asn Gln Ala Arg Ile Glu Glu Leu
1105                1110                1115                1120

Glu Glu Glu Leu Glu Ala Glu Arg Thr Ala Arg Ala Lys Val Glu Lys
                1125                1130                1135

Leu Arg Ser Asp Leu Ser Arg Glu Leu Glu Glu Ile Ser Glu Arg Leu
            1140                1145                1150

Glu Glu Ala Gly Gly Ala Thr Ser Val Gln Ile Glu Met Asn Lys Lys
            1155                1160                1165

Arg Glu Ala Glu Phe Gln Lys Met Arg Arg Asp Leu Glu Glu Ala Thr
        1170                1175                1180

Leu Gln His Glu Ala Thr Ala Ala Ala Leu Arg Lys Lys His Ala Asp
1185                1190                1195                1200
```

-continued

```
Ser Val Ala Glu Leu Gly Glu Gln Ile Asp Asn Leu Gln Arg Val Lys
            1205                1210                1215

Gln Lys Leu Glu Lys Glu Lys Ser Glu Phe Lys Leu Glu Leu Asp Asp
        1220                1225                1230

Val Thr Ser Asn Met Glu Gln Ile Ile Lys Ala Lys Ala Asn Leu Glu
    1235                1240                1245

Lys Val Ser Arg Thr Leu Glu Asp Gln Ala Asn Glu Tyr Arg Val Lys
1250                1255                1260

Leu Glu Glu Ala Gln Arg Ser Leu Asn Asp Phe Thr Thr Gln Arg Ala
1265                1270                1275                1280

Lys Leu Gln Thr Glu Asn Gly Glu Leu Ala Arg Gln Leu Glu Glu Lys
            1285                1290                1295

Glu Ala Leu Ile Ser Gln Leu Thr Arg Gly Lys Leu Ser Tyr Thr Gln
        1300                1305                1310

Gln Met Glu Asp Leu Lys Arg Gln Leu Glu Glu Glu Gly Lys Ala Lys
    1315                1320                1325

Asn Ala Leu Ala His Ala Leu Gln Ser Ala Arg His Asp Cys Asp Leu
    1330                1335                1340

Leu Arg Glu Gln Tyr Glu Glu Glu Thr Glu Ala Lys Ala Glu Leu Gln
1345                1350                1355                1360

Arg Val Leu Ser Lys Ala Asn Ser Glu Val Ala Gln Trp Arg Thr Lys
            1365                1370                1375

Tyr Glu Thr Asp Ala Ile Gln Arg Thr Glu Glu Leu Glu Glu Ala Lys
        1380                1385                1390

Lys Lys Leu Ala Gln Arg Leu Gln Asp Ala Glu Glu Ala Val Glu Ala
    1395                1400                1405

Val Asn Ala Lys Cys Ser Ser Leu Glu Lys Thr Lys His Arg Leu Gln
    1410                1415                1420

Asn Glu Ile Glu Asp Leu Met Val Asp Val Glu Arg Ser Asn Ala Ala
1425                1430                1435                1440

Ala Ala Ala Leu Asp Lys Lys Gln Arg Asn Phe Asp Lys Ile Leu Ala
            1445                1450                1455

Glu Trp Lys Gln Lys Tyr Glu Glu Ser Gln Ser Glu Leu Glu Ser Ser
        1460                1465                1470

Gln Lys Glu Ala Arg Ser Leu Ser Thr Glu Leu Phe Lys Leu Lys Asn
    1475                1480                1485

Ala Tyr Glu Glu Ser Leu Glu His Leu Glu Thr Phe Lys Arg Glu Asn
    1490                1495                1500

Lys Asn Leu Gln Glu Glu Ile Ser Asp Leu Thr Glu Gln Leu Gly Glu
1505                1510                1515                1520

Gly Gly Lys Asn Val His Glu Leu Glu Lys Val Arg Lys Gln Leu Glu
            1525                1530                1535

Val Glu Lys Leu Glu Leu Gln Ser Ala Leu Glu Glu Ala Glu Ala Ser
        1540                1545                1550

Leu Glu His Glu Glu Gly Lys Ile Leu Arg Ala Gln Leu Glu Phe Asn
    1555                1560                1565

Gln Ile Lys Ala Glu Ile Glu Arg Lys Leu Ala Glu Lys Asp Glu Glu
    1570                1575                1580

Met Glu Gln Ala Lys Arg Asn His Gln Arg Val Val Asp Ser Leu Gln
1585                1590                1595                1600

Thr Ser Leu Asp Ala Glu Thr Arg Ser Arg Asn Glu Val Leu Arg Val
            1605                1610                1615

Lys Lys Lys Met Glu Gly Asp Leu Asn Glu Met Glu Ile Gln Leu Ser
```

```
                        1620           1625            1630
His Ala Asn Arg Met Ala Ala Glu Ala Gln Lys Gln Val Lys Ser Leu
            1635            1640            1645

Gln Ser Leu Leu Lys Asp Thr Gln Ile Gln Leu Asp Asp Ala Val Arg
    1650            1655            1660

Ala Asn Asp Asp Leu Lys Glu Asn Ile Ala Ile Val Glu Arg Arg Asn
1665            1670            1675            1680

Asn Leu Leu Gln Ala Glu Leu Glu Glu Leu Arg Ala Val Val Glu Gln
            1685            1690            1695

Thr Glu Arg Ser Arg Lys Leu Ala Glu Gln Glu Leu Ile Glu Thr Ser
    1700            1705            1710

Glu Arg Val Gln Leu Leu His Ser Gln Asn Thr Ser Leu Ile Asn Gln
    1715            1720            1725

Lys Lys Lys Met Glu Ser Asp Leu Thr Gln Leu Gln Ser Glu Val Glu
    1730            1735            1740

Glu Ala Val Gln Glu Cys Arg Asn Ala Glu Glu Lys Ala Lys Lys Ala
1745            1750            1755            1760

Ile Thr Asp Ala Ala Met Met Ala Glu Glu Leu Lys Lys Glu Gln Asp
            1765            1770            1775

Thr Ser Ala His Leu Glu Arg Met Lys Lys Asn Met Glu Gln Thr Ile
            1780            1785            1790

Lys Asp Leu Gln His Arg Leu Asp Glu Ala Glu Gln Ile Ala Leu Lys
    1795            1800            1805

Gly Gly Lys Lys Gln Leu Gln Lys Leu Glu Ala Arg Val Arg Glu Leu
    1810            1815            1820

Glu Gly Glu Leu Glu Ala Glu Gln Lys Arg Asn Ala Glu Ser Val Lys
1825            1830            1835            1840

Gly Met Arg Lys Ser Glu Arg Arg Ile Lys Glu Leu Thr Tyr Gln Thr
            1845            1850            1855

Glu Glu Asp Lys Lys Asn Leu Leu Arg Leu Gln Asp Leu Val Asp Lys
            1860            1865            1870

Leu Gln Leu Lys Val Lys Ala Tyr Lys Arg Gln Ala Glu Glu Ala Glu
    1875            1880            1885

Glu Gln Ala Asn Thr Asn Leu Ser Lys Phe Arg Lys Val Gln His Glu
    1890            1895            1900

Leu Asp Glu Ala Glu Glu Arg Ala Asp Ile Ala Glu Ser Gln Val Asn
1905            1910            1915            1920

Lys Leu Arg Ala Lys Ser Arg Asp Ile Gly Ala Lys Gln Lys Met His
            1925            1930            1935

Asp Glu Glu

<210> SEQ ID NO 2
<211> LENGTH: 19
<212> TYPE: PRT
<213> ORGANISM: mouse

<400> SEQUENCE: 2

Asp Ser Ala Phe Asp Val Leu Ser Phe Thr Ala Glu Glu Lys Ala Gly
1               5                   10                  15

Val Tyr Lys

<210> SEQ ID NO 3
<211> LENGTH: 15
<212> TYPE: PRT
<213> ORGANISM: mouse
```

-continued

```
<400> SEQUENCE: 3

Leu Glu Asp Ala Arg Arg Leu Lys Ala Ile Tyr Glu Lys Lys Lys
1               5                   10                  15
```

INVOLVEMENT OF AUTOANTIGENS IN CARDIAC GRAFT REJECTION

BACKGROUND OF THE INVENTION

Heart transplantation is a life-saving procedure for patients with incurable chronic cardiac diseases. However, immunological rejection remains the main obstacle to long-term survival of cardiac transplants. Three years after transplantation, nearly 30% of the cardiac grafts are rejected. Despite recent advances in immunosuppressive therapy, such treatment is often non-specific and often associated with increased risks of infection and cancer in transplanted patients. In addition, it is generally poorly effective in preventing chronic rejection. Consequently, it is crucial to design selective antigen-specific therapies to achieve long lasting immune tolerance to donor organs; a task that requires elucidation of the cellular and molecular mechanisms underlying the allograft rejection process.

Acute rejection is generally regarded as rejection occurring within the first six months of transplantation. Acute rejection can be diagnosed relatively easily, for example, in the case of a cardiac transplant by the appearance of certain cell types in biopsy cell infiltrate. Chronic rejection, generally regarded as that occurring at least six months after transplantation, is very difficult to diagnose clinically, and may not manifest itself clearly for some years, by which time treatment is generally unsuccessful.

In chronic rejection there is typically found to be vasculopathy in the rejected organ, and the coronary artery disease known as "accelerated" or "transplant-associated" coronary artery disease. A number of risk factors, e.g. numbers of acute rejection episodes, type of immunosuppression, serum lipid levels, viral infections, etc., contribute to the development of this serious chronic complication following cardiac transplantation. Strategies for blocking T-cell costimulation may help prevent chronic rejection in clinical transplantation.

The contractile proteins found in cardiac muscle, which include myosin heavy and light chains, have particular significance for cardiac performance. The expression of these proteins correlates with development of the tissues. The initial formation of skeletal muscle fibers is accompanied by the expression of muscle-type actin and myosin genes. Genes expressed in adult cardiac tissue are coexpressed with the corresponding skeletal muscle sequence during fetal development. During subsequent maturation of muscle fibers in vivo, developmental changes in the expression of fetal/adult isoforms of these proteins occur, shifting to the cardiac forms.

Two types of myosin heavy chain (MYHC) are expressed in the mammalian heart, $\alpha$- and $\beta$-MYHC; and the contractile velocity of the heart is correlated with the relative amount of each MYHC. The $\alpha$-MYHC has a high ATPase activity than $\beta$-MYHC, and while hearts expressing more $\alpha$-MYHC have a more rapid contractile velocity, hearts with more $\beta$-MYHC allow for greater economy in force generation. The MYHC composition of the ventricular myocardium of humans has been reported to be greater than 95% $\beta$-MYHC. The $\alpha$-MYHC gene is expressed also in a trial muscle and the $\beta$-MYHC gene in skeletal slow-twitch muscle.

During graft rejection, there is tissue damage and cell death, which results in the cellular proteins being released into the bloodstream, including contractile proteins. The use of antimyosin antibodies has therefore been applied to determine whether there is ongoing myocarditis, myocardial infarction, or cardiac rejection in a patient (see Schutz et al. (1997) *Ann Thorac Surg* 63(2):578–81 for a review). Antimyosin scintigraphy after the application of indium 111-labeled antimyosin antibodies is a useful tool to detect or exclude noninvasively cardiac rejection in adults and children.

The current methods of heart transplantation result in rejection of a significant proportion of the grafts. Methods of preventing and diagnosing rejection are of great clinical interest.

Relevant Literature

The role indirect allorecognition during transplant rejection is reviewed by Benichou et al. (1997) *Immunol Today* 18(2):67–71. Although the initial indirect alloresponse is limited to a few dominant determing on donor major histocompatibility complex (MHC) molecules, subsequent spreading to additional determinants on recipient and donor antigens is common. Fedoseyeva et al. (1996) *Transplantation* 61(5):679–683 show that the breakdown of tolerance to an MHC self-peptide resulted from the presentation of the donor crossreactive peptide at the surface of recipient antigen-presenting cells.

SUMMARY OF THE INVENTION

Methods are provided for the improved diagnosis and prevention of allograft rejection associated with heart transplantation. A loss of tolerance to autologous contractile proteins expressed in cardiac cells, e.g. cardiac myosin heavy chain alpha, is shown to be a factor in the development of cellular immunity against an engrafted allogeneic heart. The detection of host T cells that are immunoreactive with such autologous proteins is useful as a diagnostic for development of chronic rejection in a heart recipient. Methods are also provided for tolerizing the host and for maintaining existing tolerance of cardiac proteins, in order to improve the long term survival of heart transplants.

DESCRIPTION OF THE SPECIFIC EMBODIMENTS

Figure 1:
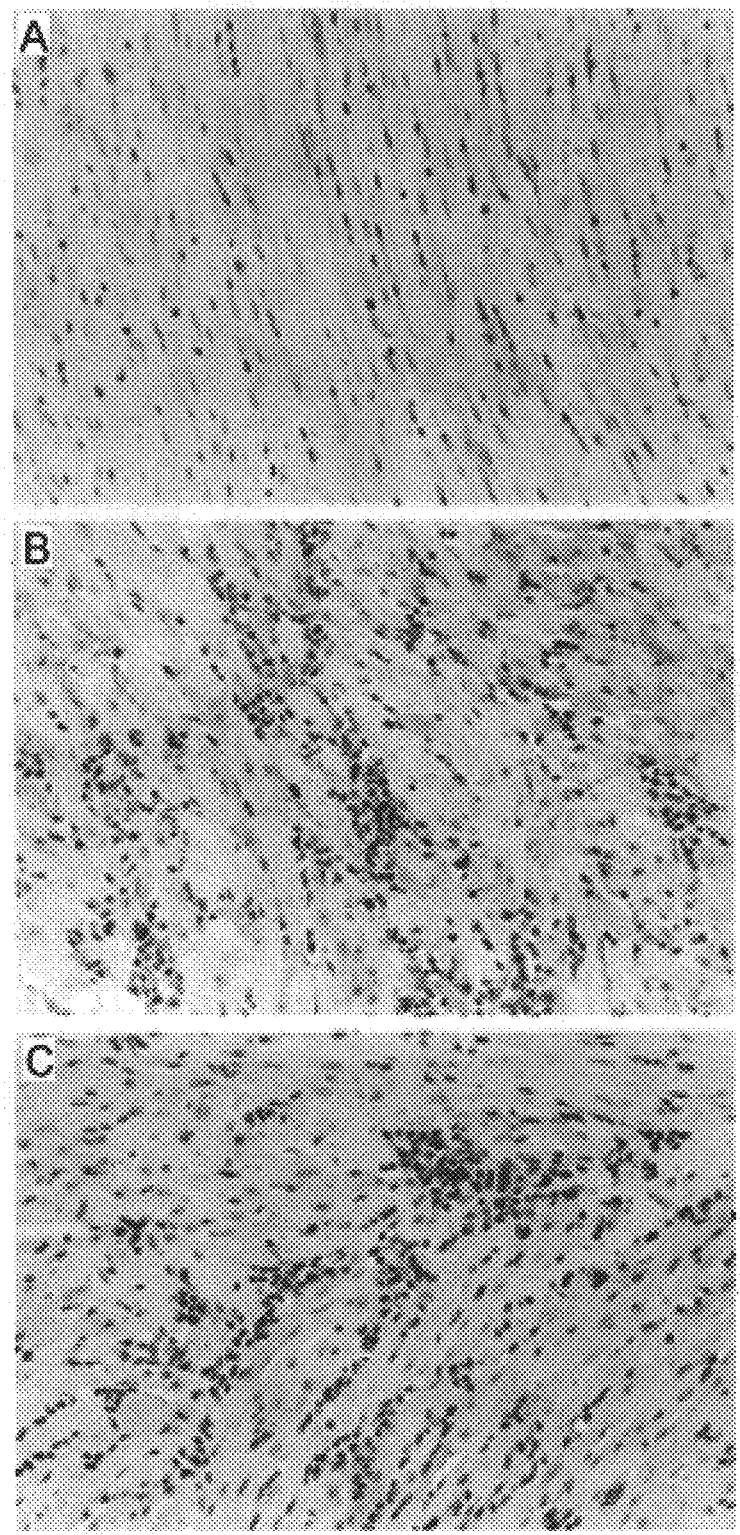
FIGS. 1A–C show the histopathology of cardiac allografts and hearts from mice with EAM.

The diagnosis and treatment of cardiac graft rejection is improved by the use of immunogenic peptides and polypeptides derived from autologous contractile proteins. A loss of tolerance to proteins expressed in cardiac cells, e.g. cardiac $\alpha$-myosin heavy chain, is shown to be a factor in the development of rejection of a transplanted heart. The detection of host T cells that are immunoreactive with such autologous proteins is useful as a diagnostic to determine the existence and extent of chronic rejection in a heart recipient. Methods are also provided for increasing the host tolerance for transplanted cardiac tissue, e.g. by polarizing the T cell response to TH2 type cells; by clonal deletion or anergy of reactive T cells; and by the use of peptide analogs to manipulate the T cell response. Blocking autoimmune responses to key tissue-antigens, such as cardiac myosin in heart transplantation, are an important therapeutic approach to achieve immune tolerance to donor cells and subsequent long-term transplant survival.

The present invention is based on the finding that an organ specific autoantigen, such as cardiac myosin, is a target for T cell mediated acute and/or chronic graft rejection. Chronic rejection is therefore found to be influenced by the loss of tolerance to autologous polypeptide sequences. Following allotransplantation, T cell responses to donor antigens can spread to crossreactive determinants on self-proteins, thus perpetuating and amplifying the rejection process. This antigen spreading has also been implicated in tissue-specific autoimmune disorders.

Measurements of the frequency and phenotype of T cells involved in direct and indirect alloresponses demonstrate that this T cell response is mediated only by T cells belong to the TH1, IL-2/γ IFN secreting subpopulation. Treatments that block cardiac myosin-specific TH1 cells and/or promote their counterpart TH2 cells are utilized to drive the immune response to allograft towards tolerance.

DEFINITIONS

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims. As used herein the singular forms "a", "and", and "the" include plural referents unless the context clearly dictates otherwise. Thus, for example, reference to "a cell" includes a plurality of such cells and reference to "the cell" includes reference to one or more cells and equivalents thereof known to those skilled in the art, and so forth. All technical and scientific terms used herein have the same meaning as commonly understood to one of ordinary skill in the art to which this invention belongs unless clearly indicated otherwise.

Transplantation: by transplantation it is meant that donor tissue is joined with the graft recipient's body. Grafts include the transplantation of cells, tissues and organs, such as the transfusion of blood or blood components, the grafting of bone, skin, bone marrow, etc., and the transplantation of tissues of the eye, pancreas, liver, kidney, heart, brain, bowel, lung, etc. Of interest are transplantation of hearts, which may be performed in conjunction with the transplantation of other tissues, e.g. lungs, blood, etc. As used herein, a graft recipient is an individual to whom tissue or cells from another individual (donor), commonly of the same species, has been transferred. However, xenogeneic, e.g. pig, baboon, etc., tissue, cells or organs may also be involved. Generally the MHC antigens, which may be Class I or Class II will be matched, although one or more of the MHC antigens may be different in the donor as compared to the recipient. The graft recipient and donor are generally mammals, preferably human. Laboratory animals, such as rodents, e.g. mice, rats, etc. are of interest for drug screening, elucidation of immune pathways, testing peptides, etc.

Immunologically reactive T cells: Following allotransplantation, T cells present in the graft recipient may respond to histocompatibility antigens present on the donor cells. The effect of the responsiveness will depend on the type of T cells, e.g. Th1 type helper cells may express pro-inflammatory cytokines; Th2 type helper T cells express suppressive cytokines; and cytotoxic T cells express perforin, granzymes, and other proteins associated with killing of target cells. The initial response is generally directed to donor MHC antigens, either through direct or indirect allorecognition. In direct allorecognition, the recipient T cells recognize determinants on the intact donor MHC molecules displayed on transplanted cells. In indirect allorecognition, donor MHC molecules are processed and presented as peptides associated with the recipient MHC, on recipient antigen presenting cells.

Antigen spreading is a feature of T cell response during long term graft rejection. While the initial indirect T cell alloresponse may be limited to a single dominant peptide on donor MHC, during long term and chronic rejection the T cell responsiveness spreads to others, formerly cryptic determinants. The present invention demonstrates that determinants of cardiac proteins such as myosin heavy chain alpha, that are tolerated in the naive host, become T cell targets during rejection.

It is known from vaccination studies with foreign proteins that initial T cell responses are restricted to few dominant determinants on the protein, while cryptic determinants are revealed only after peptide immunization; a phenomenon called immunodominance. Autologous proteins are also comprised of dominant and cryptic determinants. Autoreactive T cells recognizing cryptic self-peptides can escape thymic elimination in neonates (see Benichou et al. (1990) J.E.M. 172:1341–1346). However, during the course of chronic and/or long term graft rejection, spreading of T cell responses to cryptic self-peptides contribute to amplification of the disease.

Cardiac tissue polypeptides: During heart transplantation, antigens of particular interest during long term graft rejection are polypeptides expressed in cardiac tissue. Such polypeptides include contractile proteins, which may be specifically or preferentially expressed in cardiac tissue. Specifically expressed polypeptides are generally found in cardiac tissue at levels at least about 10 fold greater than other tissue, e.g. skeletal muscle tissue; and may be expressed at levels at least about 100 fold higher, or greater in cardiac tissue. Preferentially expressed polypeptides are generally found at increased levels in cardiac tissue, at least about 2 fold greater than in other tissues. In some cases, the relative expression levels of the cardiac specific isoform will change during development, and under stress.

Tissue antigens of particular interest for the subject methods are the two types of myosin heavy chain (MYHC) that are expressed in the mammalian heart, α- and β-MYHC, particularly the cardiac specific isoform, α-MYHC. For convenience, the amino acid sequence of human α-MYHC is provided as SEQ ID NO:1. A number of other proteins are also involved in the contractile apparatus of cardiac muscle. These include the two pairs of muscle myosin light chains, which are known as essential light chains and regulatory light chains. The light chains stabilize the long alpha helical neck of the myosin head. Myosin light chain-2 (MYL2) is an important protein in the regulation of myosin ATPase activity in smooth muscle. Cardiac myosin-binding protein C is arrayed transversely in sarcomere A-bands and binds myosin heavy chain in thick filaments and titin in elastic filaments. The troponin complex is located on the thin filament of striated muscle and is composed of 3 component polypeptides: troponin T, troponin I, and troponin C. Three troponin T genes have been described, one of which encodes a cardiac specific isoform. Another contractile protein found in cardiac tissue is tropomyosin, which is associated with the actin filaments of myofibrils. Four known tropomyosin genes code for diverse isoforms that are expressed in a tissue-specific manner and regulated by an alternative splicing mechanism, including a striated muscle isoform that is expressed in both cardiac and skeletal muscle tissues.

The nucleotide and amino acid sequences of contractile proteins found in the heart may be accessed through public databases, including Genbank. Other information may be found in Online Mendelian Inheritance in Man, OMIM (TM). Johns Hopkins University, Baltimore, Md. MIM Number: 160710, cardiac myosin heavy chain alpha; (MYH6); MIM Number: 160760, cardiac myosin heavy chain beta (MYH7); MIM Number: 600958, cardiac myosin-binding protein c (MYBPC3); MIM Number: 160781, regulatory ventricular myosin light chain (MYL2); MIM Number: 160790; ventricular and skeletal slow myosin light chain (MYL3); MIM Number: 102540. Kurabayashi et al. (1988) *J. Clin. Invest.* 82: 524–531 describes the molecular cloning and characterization of human cardiac alpha- and beta-form myosin heavy chain cDNA clones, and the regulation of expression during development and pressure overload in human atrium.

These nucleic acid sequences may be employed for producing all or portions of the encoded polypeptides. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region.

The peptide may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the gene in eukaryotic cells, where the protein will benefit from native folding and post-translational modifications. Small peptides can also be synthesized in the laboratory. Peptides that are subsets of the complete sequence may be used to identify and investigate parts of the protein important for function, or to raise antibodies directed against these regions.

DIAGNOSTIC METHODS

For diagnostic purposes, recipients of a transplanted heart are monitored for the presence of T cells reactive with cardiac contractile proteins. The presence of such reactive T cells, particularly where the cells are of the TH1 type, or are cytotoxic T cells, indicates the presence of an on-going immune response against the transplanted tissue, and an increased probability of chronic rejection. One assay of interest is a comparison of the level of reactivity at different time points after transplantation. The antigen used in the assays may be the complete protein, or peptides derived therefrom, usually such peptides will be at least about 12 amino acids in length. A subset of peptides may be prepared, or a mixture that encompasses the complete sequence. Exemplary is the use of cardiac α-myosin heavy chain peptides.

The diagnosis may determine the level of reactivity, e.g. based on the number of reactive T cells found in a sample, as compared to a negative control from a naive host, or standardized to a data curve obtained from one or more transplant recipients. In addition to detecting the qualitative and quantitative presence of cardiac auto-antigen reactive T cells, the T cells may be typed as to the expression of cytokines known to increase or suppress inflammatory responses. While not necessary for diagnostic purposes, it may also be desirable to type the epitopic specificity of the reactive T cells, particularly for use in therapeutic administration of peptides.

T cells may be isolated from patient peripheral blood, lymph nodes, or from the site of the transplanted tissue. Reactivity assays may be performed on primary T cells, or the cells may be fused to generate hybridomas. Such reactive T cells may also be used for further analysis of disease progression, by monitoring their in situ location, T cell receptor utilization, MHC cross-reactivity, etc. Assays for monitoring T cell responsiveness are known in the art, and include proliferation assays and cytokine release assays. Also of interest is the ELISA spot assay, and the immunoscope technique.

Proliferation assays measure the level of T cell proliferation in response to a specific antigen, and are widely used in the art. In an exemplary assay, recipient lymph node, blood or spleen cells are obtained at one or more time points after transplantation. A suspension of from about $10^4$ to $10^7$ cells, usually from about $10^5$ to $10^6$ cells is prepared and washed, then cultured in the presence of a control antigen, and test antigens. The test antigens may be peptides of cardiac myosin, donor MHC peptides, or other autologous antigens suspected of inducing a T cell response. The cells are usually cultured for several days. Antigen-induced proliferation is assessed by the monitoring the synthesis of DNA by the cultures, e.g. incorporation of $^3$H-thymidine during the last 18 H of culture.

T cell cytotoxic assays measure the numbers of cytotoxic T cells having specificity for the test antigen. Lymphocytes are obtained at different time points after transplantation. Alloreactive cytotoxic T cells are tested for their ability to kill target cells bearing recipient MHC class I molecules associated with peptides derived from a test antigen. In an exemplary assay, target cells presenting peptides from the test antigen, or a control antigen, are labeled with $Na^{51}CrO_4$. The target cells are then added to a suspension of candidate reactive lymphocytes. The cytotoxicity is measured by quantitating the release of $Na^{51}CrO_4$ from lysed cells. Controls for spontaneous and total release are typically included in the assay. Percent specific $^{51}Cr$ release may be calculated as follows: 100×(release by CTL—spontaneous release)/ (total release—spontaneous release).

The repertoire of the reactive T cells may be analyzed using the immunoscope technique. The immunoscope technique permits the identification and the frequency measurement of all antigen specific TCR expressing individual T cell clones in unmanipulated, freshly collected T cells from the graft or recipient lymphoid organs (see Even et al. (1995) *Res. Immunol.* 146:65–80; Pannetier et al. (1995) *Immunol. Today* 16:176–81). The TCR repertoire expressed by recipient T cells from the spleen and the graft may be assessed to different antigen, e.g. cardiac myosin, peptides. The results are of interest for the design of certain therapies that utilize anti-T cell receptor reagents.

The specific T cell repertoire analysis may utilize the polymerase chain reaction performed with specific $C_\beta$ and $V_\beta$ primers. The amplification products are then analyzed by sequencing or run-off reactions. For run-off reactions and determination of relative index of stimulation (RIS), PCR products are elongated with labeled $J_\beta$ oligonucleotide primers in another PCR step (run-off). For each $V_\beta$–$J_\beta$ rearrangement, the fluorescent run-off products of various sizes that are elongated throughout the CDR3 regions can be separated on a denaturing gel and their lengths calculated by comparison with appropriate size standards. In all $V_\beta$–$J_\beta$ combinations, the elongation products will be distributed into 6–11 peaks and corresponded to in-frame transcripts. The RIS can be calculated using the following formula: RIS=[(area of one experimental peak)/(sum of areas of all other experimental peaks)/(area of corresponding control peak)/(sum of areas of all other control peaks)]. When the peak profiles from the second term of the equation are fitted so as to maximize the number of superimposed peaks, the second term is about 1. Thus, after this normalization, a simpler formula of the RIS is obtained: RIS=(area of one experimental peak/area of corresponding control peak). An increase in RIS for a peak of a given nucleotide length is directly proportional to the augmentation of RNA messengers corresponding to this particular $V_\beta$–$J_\beta$ rearrangement.

Enzyme linked immunosorbent assay (ELISA) and ELISA spot assays are used to determine the cytokine profile of reactive T cells, and may be used to monitor for the expression of such cytokines as IL-2, IL-4, IL-5, γIFN, etc. The capture antibodies may be any antibody specific for a cytokine of interest, where supernatants from the T cell proliferation assays, as described above, are conveniently used as a source of antigen. After blocking and washing, labeled detector antibodies are added, and the concentrations of protein present determined as a function of the label that is bound.

The ELISA spot technique allows the measurement of different lymphokines secreted by activated T cells at individual cell level in a polyclonal, unmanipulated, T cell suspension freshly collected from the graft or recipient lymphoid organ. This technique is extremely sensitive (1 cell per $10^6$), resolutive, and detects only antigen specific activated T cells. It is utilized to determine the exact frequency and phenotype (TH1/TH2) of antigen or alloantigen specific T cells. ELISA spot assays are performed for cytokines of interest, e.g. IL-2, IL-4, γ-IFN and IL-5 (see, for example Benichou et al. (1999) *J. Immunol.* 162(1):352–8). Plates are set up with capture antibodies, as in a conventional ELISA. Lymphocytes from the graft recipient, e.g. peripheral blood lymphocytes, splenocytes, lymph node cells, etc. are placed in each well with or without antigen, e.g. stimulator cells, stimulator cell sonicate, peptides, etc., and cultured overnight. After washing, labeled detection antibodies are added. The plate-bound secondary antibodies are then visualized. The number of spots is counted, e.g. using a computerized image analysis system that is designed to detect ELISA spots using predetermined criteria based on size, shape and colorimetric density.

The above diagnostic assays may be performed with various peptides derived from the autologous protein of interest. A series of peptides having the sequence of an auto-antigen, e.g. α-MYHC, epitope. Possible peptides are screened to determine which are immunodominant in the context of graft rejection. The specific peptides may then be used to determine the presence of a specific autoimmune response in affected patients. The peptides are also used to induce tolerogenic responses in patients, through the induction of Th2-type T cell responses, or through clonal T cell deletion or inactivation.

The immunodominant peptides are defined by screening with a panel of peptides derived from the test protein. The peptides have the amino acid sequence of a portion of the protein, usually at least about 8 and not more than about 20 amino acids in length. The panel of peptides will represent the length of the protein sequence, i.e. all residues are present in at least one peptide. Preferably overlapping peptides are generated, where each peptide is frameshifted from 1 to 5 amino acids, thereby generating a more complete set of epitopes. The peptides may be initially screened in pools, and later screened for the exact epitope to which the T cell will respond.

Various methods are known in the art for determining whether a T cell clone will respond to a particular antigenic peptide. Typically the peptide or pool of peptides is added to a suspension of the T cells for a period of from one to three days. The response of the T cells is measured by proliferation, e.g. uptake of $^3$H-thymidine, or by release of cytokines, e.g. IL-2. Various assays are available for detecting the presence of released IL-2.

Various negative and positive controls may be included in the assay, for example unrelated peptides, medium alone, antigen presenting cells expressing different HLA alleles, particularly from different species, may serve as negative controls. Positive controls may include the intact protein, or pools representing all peptides.

An alternative method relies on the detection of circulating anti-cardiac myosin antibodies in transplant recipients. Methods of detecting specific antibodies are well-known in the art. Antibodies specific for CM may be used in screening immunoassays, where an increase in CM specific antibodies is indicative of graft rejection. A sample is taken from the transplant recipient. Samples, as used herein, include biological fluids such as blood, tears, saliva, lymph, dialysis fluid and the like; organ or tissue culture derived fluids; and fluids extracted from physiological tissues. Also included in the term are derivatives and fractions of such fluids. Blood samples and derivatives thereof are of particular interest.

Measuring the concentration of cardiac myosin specific antibodies in a sample or fraction thereof may be accomplished by a variety of specific assays. In general, the assay will measure the reactivity between a patient sample, usually blood derived, generally in the form of plasma or serum. The patient sample may be used directly, or diluted as appropriate, usually about 1:10 and usually not more than about 1:10,000. Immunoassays may be performed in any physiological buffer, e.g. PBS, normal saline, HBSS, dPBS, etc.

In one embodiment, a conventional sandwich type assay is used. A sandwich assay is performed by first attaching the cardiac myosin to an insoluble surface or support. The cardiac myosin may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently.

The insoluble supports may be any composition to which cardiac myosin peptides can be bound, which is readily separated from soluble material, and which is otherwise compatible with the overall method of measuring antibodies. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Before adding patient samples or fractions thereof, the non-specific binding sites on the insoluble support i.e. those not occupied by cardiac myosin, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used.

Samples, fractions or aliquots thereof are then added to separately assayable supports (for example, separate wells of a microtiter plate) containing support-bound cardiac myosin. Preferably, a series of standards, containing known concentrations of antibodies is assayed in parallel with the samples or aliquots thereof to serve as controls.

Generally from about 0.001 to 1 ml of sample, diluted or otherwise, is sufficient, usually about 0.01 ml sufficing. Preferably, each sample and standard will be added to multiple wells so that mean values can be obtained for each. The incubation time should be sufficient for antibodies molecules to bind the insoluble cardiac myosin. Generally, from about 0.1 to 3 hr is sufficient, usually 1 hr sufficing.

After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing a second receptor specific for the patient antibodies is applied. The receptor may be any compound that binds patient antibodies with sufficient specificity such that it can be distinguished from other components present. In a preferred embodiment, second receptors are antibodies specific for patient antibodies, either monoclonal or polyclonal sera, e.g. mouse anti-human antibodies, mouse anti-dog antibodies, rabbit anti-cat antibodies, etc. Such second stage antibodies may be labeled to facilitate direct, or indirect quantification of binding. Examples of labels which permit direct measurement of second receptor binding include radiolabels, such as $^3$H or $^{125}$I, fluorescers, dyes, beads, chemilumninescers, colloidal particles, and the like. Examples of labels that permit indirect measurement of binding include enzymes where the substrate may provide for a colored or fluorescent product. In a preferred embodiment, the second receptors are antibodies labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Alternatively, the second stage may be unlabeled, and a labeled third stage is used. Examples of second receptor/second receptor-specific molecule pairs include antibody/anti-antibody and avidin (or streptavidin)/biotin. Since the resultant signal is thus amplified, this technique may be advantageous where only a small amount of antibodies is present.

After the second stage has bound, the insoluble support is generally again washed free of non-specifically bound molecules, and the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and is O-phenylenediamine, which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490–495 nm is conveniently measured with a spectrophotometer.

Generally the amount of bound antibodies detected will be compared to control samples from normal patients. The presence of increased levels of cardiac myosin specific antibodies is indicative of graft rejection, usually at least about a 10 fold increase will be taken as a positive reaction.

In some cases, a competitive assay will be used. In addition to the patient sample, a competitor to the antibodies is added to the reaction mix. The competitor and the antibodies compete for binding to the cardiac myosin. Usually, the competitor molecule will be labeled and detected as previously described, where the amount of competitor binding will be proportional to the amount of antibodies present. The concentration of competitor molecule will be from about 10 times the maximum anticipated antibodies concentration to about equal concentration in order to make the most sensitive and linear range of detection.

An alternative protocol is to provide anti-patient antibodies bound to the insoluble surface. After adding the sample and washing away non-specifically bound proteins, one or a combination of the cardiac myosin are added, where the cardiac myosin are labeled so as not to interfere with the cardiac myosin binding to the antibodies. Conveniently, fused proteins may be employed, where the cardiac myosin peptide sequence is fused to an enzyme sequence, e.g. β-galactosidase.

It is particularly convenient in a clinical setting to perform the immunoassay in a self-contained apparatus. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it the cardiac myosin, with a conjugate of an enzyme with an antibodies specific antibody employed as a reagent, generally added to the sample before application. Alternatively, the cardiac myosin may be conjugated to an enzyme, with antibodies specific antibody bound to the measurement region.

THERAPEUTIC METHODS

Peptides that are identified as involved in chronic rejection of cardiac may then be further used in therapeutic methods to circumvent the development of T cell reactivity, or to treat ongoing graft rejection by decreasing the T cell reactivity. Several approaches are useful for this purpose.

The peptide antigens may be used in the polarization of T cell responses towards TH2 type T helper cells. The population of mature CD4$^+$ T cells is comprised of two distinct subsets that are characterized by their lymphokine patterns. Following antigen stimulation, TH1 cells produce pro-inflammatory cytokines, e.g. IL-2, IL-12 and γIFN, while Th2 cells secrete suppressive cytokines, e.g. IL-4, IL-5 and IL-10. TH2 cells are involved in allergic responses and in ensuring tolerance to self-antigens. These two T cells types are antagonistic: while IL-2 and γIFN produced by TH1 cells inhibits TH2 cells, IL4 and IL-10 secreted by TH-2 T cells suppress TH1 cells. TH1 and TH2 cells also differ by the precise structure of the antigen determinant they recognize, by the dose of antigen required for their activation and by their dependence on costimulatory signals. This phenomenon makes it possible to manipulate an immune response by polarizing the T cell response toward Th1 or TH2 compartments.

Antigen specific in vivo tolerance to allografts is achieved by strategies designed to selectively promote alloreactive TH2 cells while depressing their TH1 counterparts. Intraperitoneal administration of antigens, e.g. α-myosin heavy chain proteins of peptides derived therefrom, with incomplete Freud's adjuvant (EP-IFA) results in a unipolar TH2 response that is associated with antigen-specific T cell tolerance.

Various methods for administration to induce suppressive, Th2-type T cell responses have been described, and may be employed. For example, see Mosmann and Coffman (1989) *Ann. Rev. Immunol.* 7:145–173; Tisch and McDevitt (1994) *P.N.A.S.* 91:437–438; Rabinovitch (1994) *Diabetes* 43:613–621; and Liblau et al. (1995) *Immunol. Today* 16:34–38. For example, intraperitoneal injection in incomplete Freud's adjuvant (Tian et al. (1996) *Nature Med.* 2:1348–1353); nasal administration (Wraith and Metzler (1993) *Int. Immunol.* 5:1159–1165), and oral administration (Trentham et al. (1993) *Science* 261:172701730) have all been shown to provide for a suppressive response. Low doses of soluble peptides may be preferred to induce a Th2 response.

In an alternative approach, T cell clonal inactivation or deletion of cells reactive with cardiac polypeptides may be performed. Antigen-mediated stimulation of T cells is a multi-step process in which surface receptors besides the TCR are involved. Among these receptors, CD28, which interacts with B7 on antigen presenting cells, delivers a second signal that is a prerequisite for the complete activation of T cells. In the absence of CD28/B7 interaction, T cells undergo aborted activation that does not result in proliferation or lymphokine production, and such T cells become unresponsive to further restimulation by APCs capable of delivering the proper second signal. This stage of unresponsiveness is referred to as T cell anergy. "Non-professional" antigen presenting cells, e.g. endothelial and epithelial cells (B7$^-$ cells), induce T cell anergy upon antigen presentation.

T cell anergy can lead to tolerance of allografts. This state can be achieved by depletion of professional APCs (passenger leukocytes) from the grafted tissue prior to transplantation; treatments that impair CD28/B7 interaction such as CTLA4-Ig; etc. Although the state of anergy is transient, long term graft survival is achieved. Methods of controlling the protocol of antigen administration, and by targeting antigen to certain APCs or by signaling specific TCR in an appropriate manner are used to induce T cell anergy. For example, blocking only B7-1 antigen with a specific monoclonal antibody such as B7-24 without blocking B7-2 antigen, when combined with an immunosuppressive drug such as cyclosporin A, can induce T-cell tolerance or anergy. Alternatively, peripheral T cell clonal deletion is achieved by high affinity interaction between T cells and their ligands following high dose immunization by selected routes.

Intravenous injection (IV) of large doses of antigen in a soluble form (without adjuvant) is known to induce antigen specific in vivo immune tolerance. T cell responses to MHC peptides can be tolerized via IV immunization procedures (Benichou et al. (1994) *Intl. Immunol.* 6:131). Intravenous administration of 500 μg of dominant donor peptide in saline 14 days pre-transplant was sufficient to inhibit indirect alloresponse to this donor peptide and to induce indefinite graft survival. This phenomenon is antigen specific. IV tolerization 4 days post-transplant with this donor peptide is also effective at delaying acute rejection. Early inhibition of indirect alloresponses via tolerization to dominant donor MHC peptides and autoantigens can prevent antigen spreading to cryptic determinants on donor MHC and tissue specific antigens thus delaying or reducing the severity of subsequent chronic graft rejection.

Clonal deletion/inactivation of alloreactive T cells using anti-TCR antibodies may be performed following identification of the TCRs involved in indirect alloresponses to dominant and cryptic donor MHC peptides and to organ specific autoantigen peptides (for examples, see Jewell et al. (1998) *Immunol Cell Biol.* 76(1):74–82; Zhang et al. (1995) *J Immunol.* 155(12):5868–77). In all tolerization experiments, involving IV antigen injections and anti-TCR treatments, reduction in the frequency of responding T cells along with disappearance of specific T cell clones from the TCR repertoire demonstrates peripheral T cell deletion. Alternatively, absence of ELISA spot along with unchanged T cell repertoire will demonstrate T cell inactivation. If there is a switch of T cell response towards the TH2 phenotype, this will be detected by ELISA spot assay.

Mobilization of selected T cell-interactions may be achieved by immunization with peptide analogs. Studies using analog peptides displaying amino acid substitutions at key TCR contact positions of the antigen peptide have revealed that TCR can interpret subtle modifications in its ligand, resulting in differential activation of T cell functions. Some analogs behave as antagonists of the wild-type peptide and thereby inhibit T cell signals delivered by the specific antigen. Suitable peptide analogs are based on immunogenic peptides from an autoantigen of interest, particularly α-MYHC. Peptides are administered to the recipient prior to transplantation, or after transplantation, particularly prior to development of chronic rejection.

The peptide analogs may be modified in a wide variety of ways. Sequence analogs may be prepared by oligopeptide synthesis using a stepwise substitution of the amino acids at each position with alanine or valine, particularly alanine. Generally the total number of amino acids substituted will not exceed 3, ranging from 1 to 3, usually 1 to 2. Methods of producing "scanning" mutatations are known in the art, and have been successfully used with a number of different peptides. Examples of protocols for scanning mutations may be found in Gustin, et al. (1993) *Biotechniques* 14:22; Barany (1985) *Gene* 37:111–23; Colicelli, et al. (1985) *Mol Gen Genet* 199:537–9 and Prentki, et al. (1984) *Gene* 29:303–13. The set of "scanned" peptides are then tested for responsiveness by T cell hybridomas prepared as described above.

The peptide formulation will be administered at a dosage sufficient to inhibit undesirable T cell activity. The T cells may be cytotoxic, e.g. CD8$^+$ cells, or T helper cells, e.g. CD4$^+$. In many cases it will be desirable to inhibit the activity of cytotoxic T cells. The determination of undesirable T cell activity will vary with the patient status and condition that is being treated. For suppression of graft rejection, T cell activity may be indirectly determined by survival of engrafted tissue, where increased graft survival correlates with decreased T cell activity. Other useful measures of T cell activity are the release of cytokines, e.g. IL-1, IL-2, IL-3, IL-4, IL-5, IL-6, IL-8, IL-9, IL-10, IL-13, IL-14, GM-CSF, IFNγ, LIF, TNFα, TNFβ; the presence of T cells at disease associated sites, e.g. transplanted tissue, and other measures of T cell activity as known in the art.

The level of T cell inhibition will be sufficient to reduce the severity of the disease. For example, a graft will usually survive at least about 25% longer when the recipient is treated with the subject methods, and the graft survival may be extended by as much as 50%. The subject methods are used to reduce the activity of T cells in cell cultures, and in experimental animal models as a control to study the effect of other immunosuppressants, in drug screening assays for agents that increase T cell activity, etc.

The peptides may be administered as a single active agent, or in combination with other therapeutic agents, particularly other immunosuppressants. The effect of combined immunosuppressant will generally be at least additive in the level of immunosuppression achieved with the single drugs, and may provide for a synergistic effect. Immunosuppressants of interest include cyclosporins A and G, FK-506, mycophenylate mofetil, rapamycin, azathioprine, antibodies for plasma membrane proteins associated with graft rejection, such as antibodies to CD4, CD8, CD2, LFA-1, ICAM-1, CD28, and the like; and immunosuppressive oligopeptides derived from MHC molecules.

The subject compositions may also be used ex vivo. In cases of transplantation of organs, particularly solid organs, whether xenogeneic or allogeneic, the donor organ may be bathed in a medium comprising the subject peptides. In this way, CTLs present with the organ will be inhibited from participating in graft versus host disease. Also, during the period when the subject peptides remain bound to the organ, the recipient's CTLs will be inhibited from being activated. Generally, the concentration of the peptide will vary in the medium, depending upon the activity of the peptide, the level of inhibition desired, the presence of other compounds affecting CTL activation, and the like.

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the methods and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, and pressure is at or near atmospheric.

EXPERIMENTAL

EXAMPLE 1

De novo induction of Heart Autoimmunity

It was investigated whether heart autoimmunity is induced during the rejection of cardiac allografts. Histologic examination of rejected allogeneic hearts revealed histopathological features that were strikingly similar to those observed in the hearts of mice with experimental autoimmune myocarditis (EAM). EAM in mice represents the best characterized animal model for human myocarditis, a heart disease which causes severe cardiac malfunction and ultimate failure. Cardiac myosin (CM), a contractile protein expressed exclusively in the heart, has been identified as the target autoantigen in this autoimmune disease.

The myocarditis-like histopathology of transplanted allogeneic heart is caused by immune responses to the myocarditis autoantigen, cardiac myosin. It is shown that after cardiac allograft in mice, B and T cell immune tolerance to CM self-protein is broken. Direct evidence is provided showing that post-transplant de novo autoimmune response to CM contributes to the allograft rejection process.

Results

Cardiac allograft induces autoimmune response to self-cardiac myosin, the autoantigen that causes autoimmune myocarditis. Single MHC class I allele mismatched A/J ($K^k$) and A.TL ($K^s$) mice were used either as donors or recipients in vascularized heterotopic cardiac transplant model (Neu et al. (1987) *J Immunol.* 138:2488–2492). Allogeneic hearts were consistently rejected at day 9.4±0.3 (A/J—A.TL and at day 8.6±0.5 (A.TL—A/J) after transplantation. In contrast, syngeneic grafts survived indefinitely (>100 days). Histologic examination of rejected allogeneic hearts revealed an interstitial inflammatory cell infiltrate and adjacent myocyte damage (FIG. 1b). Interestingly, we found that these histopathological features were strikingly similar to those observed in the hearts of mice with experimental autoimmune myocarditis (EAM).

Based upon this observation, we next investigated whether myocarditis-like histopathology of transplanted allogeneic heart is associated with immune responses to the known myocarditis autoantigen, cardiac myosin. To test this, T cell response to purified mouse CM was investigated in the spleen of mice transplanted with allogeneic hearts. a) Spleen cells were cultured in either medium alone (open bars) or with the following antigens: purified murine cardiac myosin (solid bars) or control antigen, hen egg-lysozyme (HEL) (dashed bars). Data are expressed as concentration of IFNγ (pg/ml). The data are representative of 3–8 mice tested individually in each group. b) Antibody responses to cardiac myosin in mice transplanted with allogeneic heart (solid bars), syngeneic heart (hatched bars) and in non-transplanted mice (open bars) are shown. Data are presented as mean absorbance at OD 405 nm±SE after subtraction of absorbance values obtained with plates coated with control antigen. Each bar shows an individual mouse, representative of 3–5 mice tested in each group.

Figure 2:
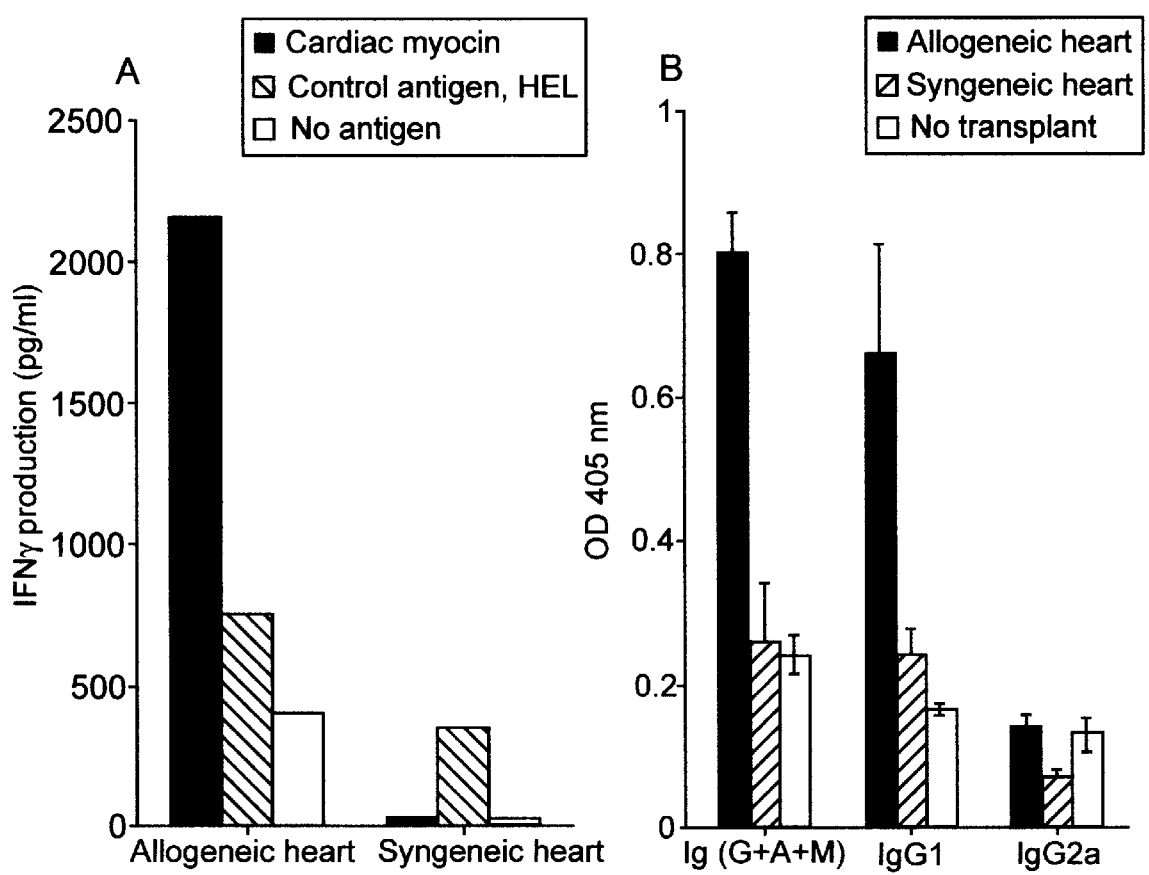
FIGS. 2A–B show the T cell and B cell responses to cardiac myosin in transplanted mice.

As shown in FIG. 2a, vigorous anti-CM T cell response, as determined by interferon-γ (IFNγ) production, was observed in mice tested 10–15 days after transplant, and it was found to be mediated by CD4+, NTHC class II (Ak)-restricted T cells. No IL-4 and IL-5 production were detected. Importantly, no anti-myosin T cell responses were observed in normal mice, or in mice grafted with syngeneic hearts (FIG. 2) and in mice that received an allogeneic skin transplant. We conclude that following cardiac allograft, T cell tolerance to CM had been disrupted, a phenomenon that resulted by de novo activation of anti-CM CD4+ autoreactive T cells displaying TH1 phenotype.

While it is firmly established that EAM is primarily mediated by autoreactive T cells, anti-CM autoantibodies have been shown to contribute to the pathogenesis associated with this disease. It was therefore important to determine whether T cell tolerance breakdown to self-CM in heart transplanted mice was also accompanied by anti-CM autoantibody production. As shown in FIG. 2b, high titers of CM-specific autoantibodies were detected in transplanted mice sera (FIG. 2b). Similar to EAM, the majority of these anti-myosin antibodies were of IgG1 isotype (FIG. 2b). No anti-myosin B cell responses were observed in normal mice, or in mice-rafted with syngeneic hearts (FIG. 2). Therefore, like in EAM, mice engrafted with an allogeneic heart display vigorous B cell autoimmune response to CM. Altogether, our observations suggested that in allogeneic heart transplanted mice, autoimmune T and B cell responses to CM is associated with a pathology that resembles that observed in EAM.

Figure 3:
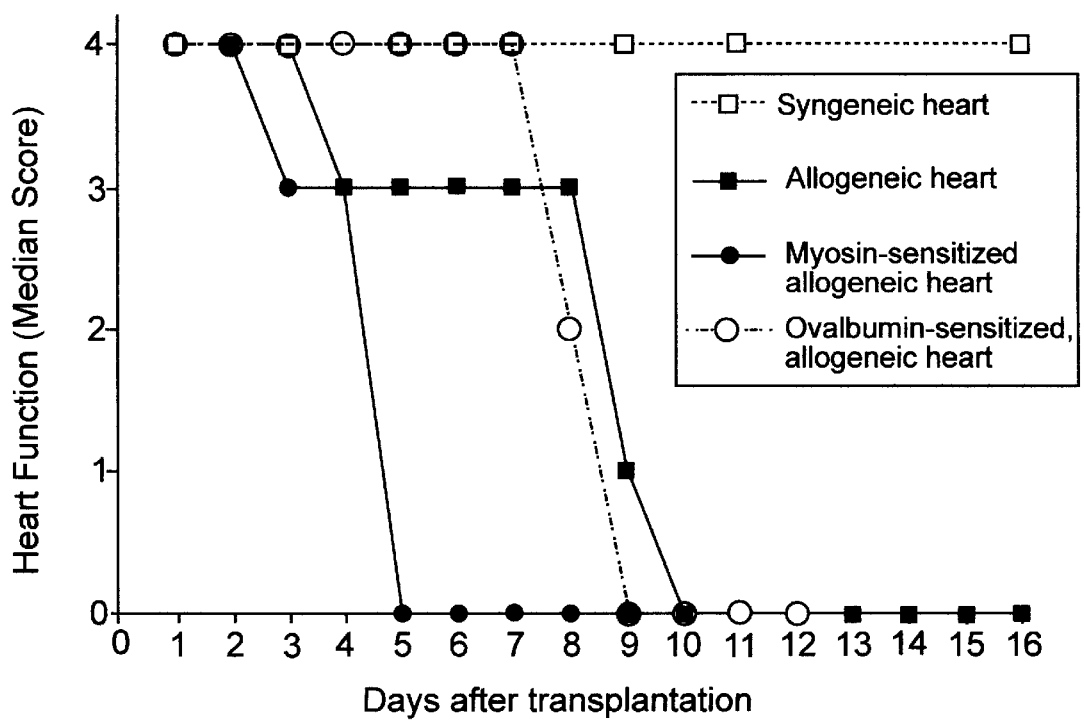
FIG. 3 is a graph showing accelerated rejection of cardiac allografts in mice sensitized with cardiac myosin.

Anti-CM autoimmune response is relevant to the rejection of cardiac transplants. Next, it was crucial to investigate whether the anti-CM autoimmune response does actually influence the allograft rejection process. To address this, we tested the effect of pre-transplant sensitization of recipients with CM on the course of cardiac transplant rejection. Recipient mice were immunized intraperitoneally with CM and then transplanted 21 days later with allogeneic hearts. As shown in FIG. 3, CM-sensitized mice rejected donor grafts in an accelerated fashion (5.2±0.6 days, p<0.001; n=5). Sensitization with a control antigen, ovalbumin, had no effect on transplant survival (9.5±0.6; n=4). Allogeneic (A/J) hearts were transplanted to untreated A.TL mice (filled squares) or to A.TL mice sensitized with either cardiac myosin (filled circles) or ovalbumin, control antigen (Boehringer Mannheim) (open circles) 21 days prior to transplantation. A.TL mice transplanted with A.TL syngeneic hearts are also shown (open squares). In sensitization experiments, mice were immunized with murine CM as described for EAM induction but in the absence of pertussis toxin. Data represent the median score of heart function (0–4) determined for 3–8 mice in each experimental croup. Heart beat intensity was graded on a scale of 0 (no palpable impulse) to 4 (strong impulse).

Figure 4:
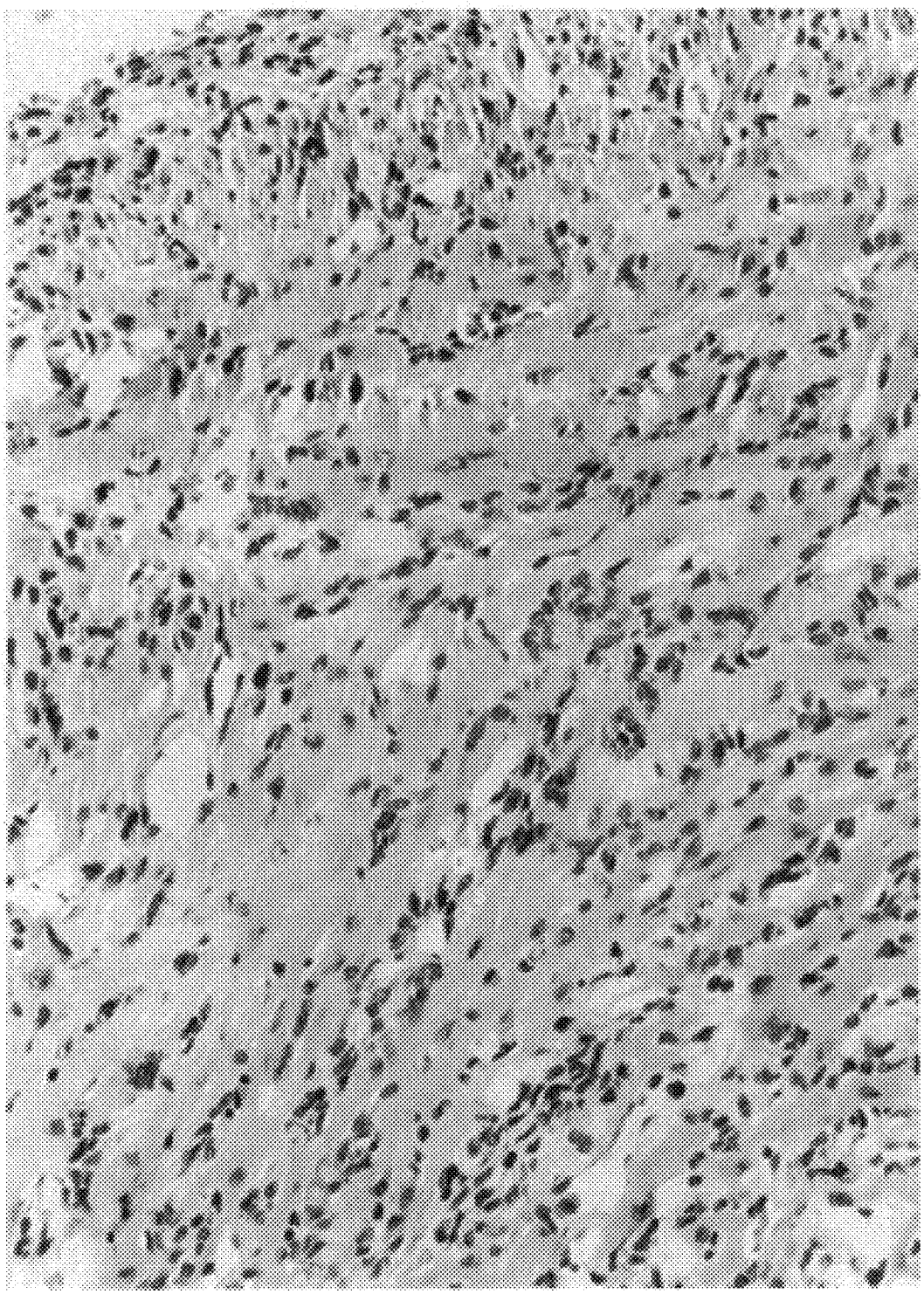
FIG. 4. shows the histopathology of syngeneic grafts from mice sensitized with CM pre-transplant.

To further demonstrate the relevance of anti-CM response in heart transplantation, we tested whether in the absence of an alloresponse, induction of anti-CM autoimmune response alone could affect cardiac graft rejection. Recipient A.TL mice were sensitized to CM and then transplanted with a syngeneic heart. Strikingly, in contrast to untreated recipients that retained syngeneic grafts indefinitely, CM-sensitized mice rejected syngeneic transplants after 40 days (Table 1). In addition, rejected syngeneic hearts displayed histopathological features that were similar to that of allogeneic transplants undergoing rejection. FIG. 4 shows a photomicrograph of a syngeneic heart from a CM-sensitized recipient mouse display a subepicardial and myocardial interstitial lymphocytic inflammatory cell infiltrate and adjacent myocyte damage. This result demonstrated that, in the absence of allogeneic stimulation, anti-myosin autoimmune response per se is sufficient to elicit graft rejection.

TABLE 1

Rejection of syngeneic cardiac transplants following pre-sensitization of recipient mice with cardiac myosin.

| Treatment | Transplant | Day of graft rejection | Mean day of graft rejection SE |
|---|---|---|---|
| None | Syngeneic | >100 (n = 3) | >100 |
| None | Allogeneic | 8, 9, 9, 9, 9, 10, 10, 11 (n = 8) | 9.4 ± 0.3 |
| OVA sensitization | allogeneic | 8, 9, 10, 11 (n = 4) | 9.5 ± 0.6 |
| CM sensitization | Allogeneic | 4, 4, 5, 6, 7 (n = 5) | 8.2 ± 0.6 |
| CM sensitization | Syngeneic | 32, 32, 33, 50, 56, 56, (n = 6) | 43.2 ± 4.9 |

In sensitization experiments, recipient mice were immunized subcutaneously in their rear footpads and intraperitoneally with 80 μg of murine cardiac myosin or control ovalbumin protein emulsified in CFA on day 0 and 7. After 21 days, sensitized mice received either syngeneic or allogeneic heterotopic heart transplants. Rejection was monitored daily by palpation analysis. Heart beat intensity was graded on a scale of 0 (no palpable impulse) to 4 (strong impulse). Rejection was determined to be the time when heart impulse declined to 1–0 for two consecutive days.

Taken together, these results show that: 1) initial response to donor NMC molecule is a prerequisite for breaking tolerance to CM and, 2) once it has been elicited, anti-CM response alone can cause the rejection of transplanted heart. Therefore, post-transplant autoimmune response to CM is likely to represent an essential element of the rejection of allogeneic cardiac transplants.

myhc α 334–352 C111-derived peptide is presented after cardiac allograft. Next, we investigated the nature of the determinant(s) on CM presented to T cells during heart allograft rejection. Previous study by Donermeyer et al. have shown that immunization of A/J mice with the peptide 334–352 of cardiac myosin heavy chain alpha (myhccc 334–352) induces EAN114. It was therefore possible that the same determinant could be involved in anti-CM autoimmune responses occurring after heart transplant.

Figure 5:
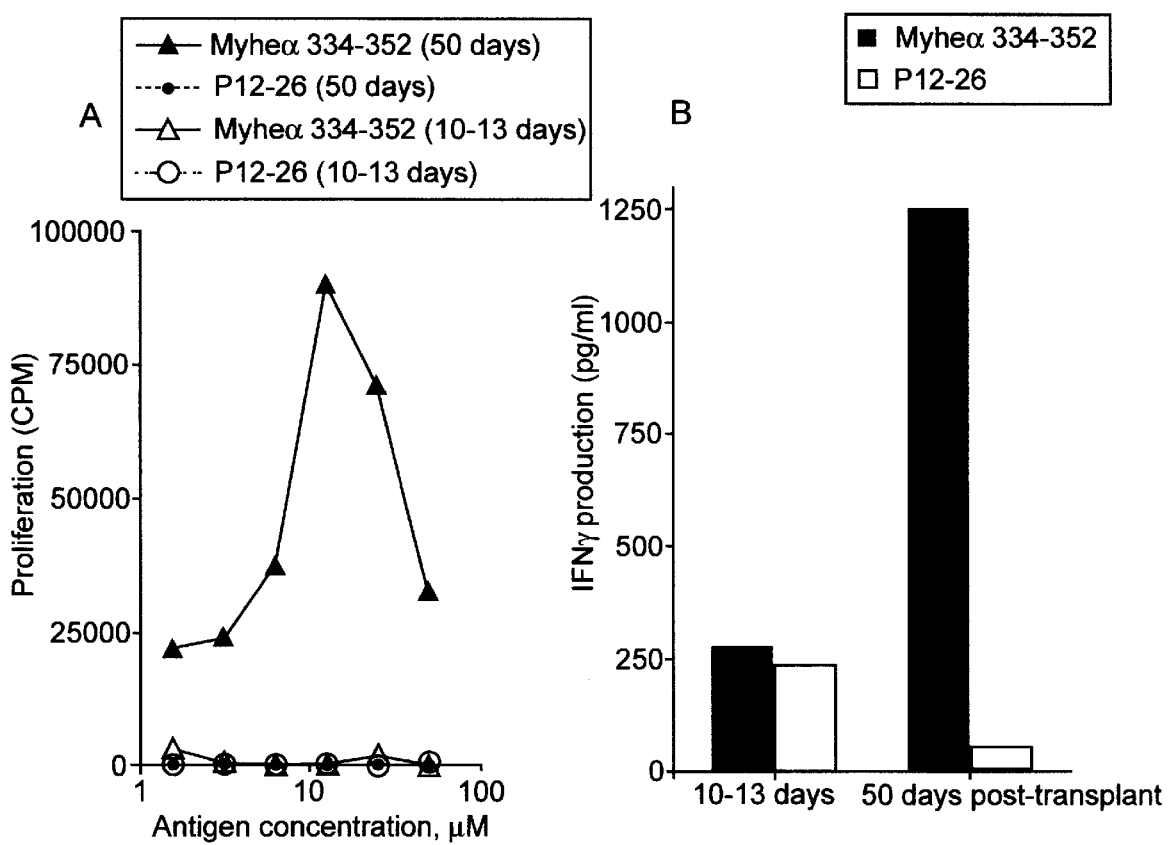
FIGS. 5A–B are graphs of the T cell response to myocarditogenic cardiac myosin peptide, myhcα 334–352 in heart-transplanted mice.

T cell proliferative response to myhcα 334–352 peptide in A.TL mice transplanted with allogeneic A/J hearts is shown in FIG. 5. Recipient spleens were removed at either 10–13 days (open symbols) or 50 days (filled symbols) following transplantation. Suspensions of spleen cells were cultured in the presence of myhcα 334–352 peptide (triangles), control λ repressor peptide, P12-26 (circles) or medium alone for 4 days. Data are expressed as delta counts per minute (CPM)

(experimental counts–medium counts). Data for individual mouse are shown, representative of 3–8 mice tested. B) myhcα 334–352 peptide-mediated recipient spleen T cell release of IFNγ was measured at 10–13 days and 50 days following heart transplantation using ELISA assay. Splenocytes were cultured for 48 hours either with myhcα 334–352 (solid bars) or control P12-26 peptide at 50 $\mu$M (open bars). Data are expressed as pg/ml of IFNγ following subtraction of control values obtained with cells cultured with medium alone. The data shown are representative of 3–5 mice tested individually in each group. When tested 10–13 days after allogeneic cardiac graft, no T cell response to myhca 334–352 peptide was detected in recipient A/J mice. However, at 50 days post-transplant, vigorous T cell response to myhcct 334–352 was observed in recipient spleens. Moreover, immunization of mice with myhcα 334–352 prior to transplantation resulted in modest but statistically significant accelerated allograft rejection (7.3±0.4 days, p<0.03; n=3).

Therefore, initial anti-CM T cell response (day 10) is apparently not directed to myhcα 334–352 peptide but to another yet unidentified CM determinant. However, at day 50 after grafting, secondary T cell response to myhcα 334–352 peptide (day 50) occurs and it may contribute to the amplification and perpetuation of the rejection process. We conclude that during long term allograft rejection, autoimmune T cell response to CM spreads to new and presumably previously cryptic determinants on CM.

Discussion

Cardiac allograft induces immune tolerance breakdown to cardiac myosin, the autoantigen that causes the heart autoimmune disease, autoimmune myocarditis. In addition, cardiac tissues from transplanted and autoimmune diseased mice display striking histological similarities. Finally, pre-transplant sensitization of recipient mice with CM causes marked acceleration of allogeneic heart grafts. Taken together, these results strongly suggest that allotransplantation-induced autoimmunity to CM contributes to cardiac graft rejection. A/J and A.TL mice have identical background genes and differ only at the K class I locus in the MHC. Since, autografts are not rejected and show no signs of autoimmunity to CM, we conclude that anti-MHC class I alloresponse is a prerequisite to tolerance breakdown to CM after cardiac allotransplantation. However, in allografts, while initial alloresponse to donor MHC is necessary to disrupt tolerance to CM, once anti-CM autoimmunity has been induced it is sufficient alone to mediate the rejection of the cardiac transplant. This is confirmed by the fact that CM-sensitized mice reject autografts in the absence of alloresponse.

Two non-mutually exclusive mechanisms may explain how the autoimmune process is triggered by the alloresponse: 1) Inflammatory cytokines produced by activated alloreactive T cells at the site of the graft may upregulate the presentation of existing CD4/MHC class II complexes and induce the expression of costimulatory molecules on cardiac antigen-presenting cells (APCs). Efficient presentation of myocarditogenic CNI determinants in the transplanted heart may lower the threshold required for activation of formerly silent CM-specific autoreactive T lymphocytes. 2) Alternatively, myocardial damage by alloreactive T cells may cause the release of circulating cardiac myosin. De novo exogenous processing of extracellular autoantigen by recipient APCs in peripheral lymphoid organs or in the grafted heart might result in the presentation of new CM determinants thus sensitizing myocarditogenic T cells.

A previous study by Donermeyer et al showed that injection with cyanogen bromide-derived CM fragments in mice induces a T cell response to myhcα 334–352 peptide on CM14. In the same study, immunization with this peptide was shown to be sufficient to mediate EAM. In our model, at day 10, no T cell response to myhcα 334–352 peptide could be detected in transplanted mice while strong autoimmune response to CM were measured. This indicates that in transplanted mice, initial anti-CM immune response is directed to determinants other than the myhcα 334–352 peptide. However, diversification of T cell response to myhcα 334–352 self-peptide occurs at a later time point (50 days) after transplantation. Therefore, antigen spreading, a phenomenon previously described in autoimmune diseases such as multiple sclerosis and insulin dependent diabetes (IDDM), is also a feature of T cell response to CM determinants during cardiac graft rejection.

It is noteworthy that allotransplanted mice bear two fully vascularized hearts, their original heart and the transplanted hearts located in the thoracic and abdominal cavities respectively. Interestingly, we observed focal inflammatory cell infiltration and some subepicardial calcification in recipient own original hearts at late time points after allogeneic transplantation (50 days post-transplant). This suggests that the autoimmune response induced in the allotransplanted heart had spread to the recipient's original heart and initiated tissue injury. Whether, in the absence of allogeneic response and inflammation the recipient's original heart would be rejected by anti-CM autoreactive T cells like a transplant remains to be determined.

In our model, CM is identical between donor and recipient mice and it therefore does not represent a minor histocompatibility antigen. No autoimmunity to CM was observed in recipient mice that received a skin allograft showing that both anti-donor NIHC alloresponse and the presence of the relevant tissue-specific autoantigen in the transplant are necessary for the induction of anti-CM autoimmune response. Previous studies have provided evidence for the involvement of tissue specific antigens shared by hosts and donors in allotransplant rejection 18-20. However, little information exists about their nature and the degree of their involvement in the rejection process. Our study clearly identifies a tissue specific protein and establishes its contribution to allograft rejection. It is likely that anti-CM autoreactive responses account for the following clinical observations in heart transplant patients: 1) Patients originally diagnosed with chronic myocarditis experience more frequent and severe rejection episodes than patients with other heart diseases2I. 2) An increase in the amounts of circulating CM following transplantation is associated with poor prognosis for cardiac transplant survival. Thus, heart transplantation-induced anti-CM autoimmunity is clinically relevant. Moreover, our data highlight the need for monitoring this response as a diagnostic indicator of rejection.

Induction of autoimmunity may represent a general phenomenon in allotransplantation. Tissue-antigens known to induce autoimmune disease, such as glutamic acid decarboxylase (IDDM) and type IV collagen (Goodpastures syndrome), could also be involved in the rejection of donor islets and kidney transplants, respectively. Therefore, pathologies observed in transplanted patients and often diagnosed as recurrent autoimmune diseases may instead be the result of de novo autoimmunity caused by the transplantation itself. While T cell response to donor MHC alloantigens initiates graft rejection, secondary autoreactive responses to some organ-specific antigens is likely to perpetuate and amplify the immune destruction of transplanted tissues. This implies that, in addition to the inhibition of T cell responses to donor MHC molecules, blocking of autoimmune responses to key tissue-antigens, such as cardiac myosin in heart transplantation, may represent a necessary therapeutic approach to achieve immune tolerance to donor cells and subsequent long-term transplant survival.

Methods

Mouse heart transplants. The A/J (Kk Ak Ek. Dd) and A.TL (Ks Ak Ek Dd) mice were obtained from the Jackson Laboratory (Bar Harbor, NTE). The care of all animals involved in this study was in accordance with institutional guidelines. Vascularized heterotopic cardiac transplantation was performed as described by Corry et al (1973) Transplantation 16:343–50. Briefly, mice were anesthetized with pentobarbital Injected intraperitoneally (2 mg/mouse) and used either as donors or recipients. The aorta and pulmonary artery are ligated and transected 0.8 to 1.5 mm from the vessel origins. The heart is lifted up and a single 7-0 silk ligature placed around the pulmonary veins prior to final division. The heart will be then stored in heparinized saline at 4° C. while the recipient mouse is prepared. The recipient's abdomen is prepared using sterile technique and is opened via a midline incision. The inferior vena cava and aorta are exposed below the renal vessels by dissecting the overlying peritoneum with cotton wool-tipped applicators. The infrarenal aorta and vena cava are clamped together with a curved pediatric hemostat. The donor heart is placed transversely in the right side of the abdominal cavity of the recipient. An end-to side anastomosis of the donor aorta to the recipient's aorta is performed. The pulmonary artery is anastomosed end-to-side to the inferior vena cave. The posterior wall of anastomosis is sutured with continuous 11-0 nylon suture from within the vessels, and then the anterior wall of the anastomosis is completed with a continuous suture externally. Finally, the abdominal wall is closed in two layers with 5-0 prolene suture.

The function of transplanted hearts was monitored daily by palpation through the abdominal wall. Heart beat intensity was graded on a scale of 0 (no palpable impulse) to 4 (strong impulse). Rejection was determined to be the time when heart impulse declined to 1–0 for two consecutive days. Statistical analysis was performed using paired t-test.

Peptides. Peptides were synthesized utilizing Fmoc chemistry by Research Genetics, Inc. (Huntsville, Ala.) and purified by HPLC (purity>95%). The amino acid sequences of the peptides were as follows: myhcα 334–352: DSAFDVLSFTAEEKAGVYK SEQ ID NO: 2; P12-26: LEDARRLKAIYEKKK SEQ ID NO: 3.

Histology. At the time of rejection, mice were sacrificed, then donor hearts were removed, fixed in neutral buffered formalin (Sigma, St. Louis, Mo.) and embedded in paraffin. Several cross-sections of each heart in the atrial-apical axis were then prepared. Sections were stained with hematoxylin and eosin.

Induction of Experimental Autoimmune Myocarditis. To induce EAM, mice were injected into rear footpads and intraperitoneally with 80 μg of murine cardiac myosin emulsified in Complete Freud's Adjuvant (CFA) on day 0 and 7. Mice also received a single intraperitoneal injection of 500 ng of pertussis toxin (List Biologicals, Detroit, Mich.) on day 0. Murine cardiac myosin was purified as described by Schiverick et al (1975) Biochim Biophys Acta. 393:124–133. The purity of preparations (>95%) was determined by SDS-PAGE. The myosin concentration was assessed spectrophotometrically using BCA Protein Assay kit (Pierce, Rockford, Ill.). Myosin was dissolved in 50 mM sodium pyrophosphate and stored at −80 C.

Cytokine measurement. At the time of rejection (10–13 days post-transplant), spleens were harvested from recipient A/J mice transplanted with either syngeneic (A/J) or allogeneic A.TL hearts. Suspensions of $10^6$ spleen cells were plated in 96 well dishes in ARNI-V medium (Gibco BR-L, Grand Island, N.Y.) supplemented with 1% FCS (Gemini Bioproducts, Inc., Calabases, Calif.). IFNγ production was measured using ELISA assay. Briefly, 96 well microtiter ELISA plates (Coming, Corning, N.Y.) were coated with capturing rat anti-mouse IFNγ monoclonal antibody (mAb), R4-6A2 (Pharmingen, San Diego, Calif.), at 1 μg/ml in bicarbonate coating buffer, pH 8.2 and incubated overnight at 4° C. After blocking with phosphate buffered saline (PBS) containing 2% bovine serum albumin (BSA) (Sigma), supernatants from cell cultures were added to the wells and incubated overnight at 4° C. For detection of bound IFNγ, biotinylated rat anti-mouse IFNγ mAb, XMG 1.2 (Pharmingen) was used followed by incubation with avidin D-coupled horseradish peroxidase (Vector, Burlingame, Calif.). Peroxidase activity was revealed with 2,2-Azino-bis (3-Ethylbenzthiazoline-6-Sulionic Acid) (A.BTS) tablets (Sigma) dissolved in phosphate-citrate substrate buffer, pH 5.0, containing $H_2O_2$. Absorbance was measured at 405 nm. Concentration of detected IFNγ (pg/ml) was calculated using recombinant murine IFNγ (Pharmingen) as a standard.

Detection of anti-CM serum antibodies. Mouse sera were tested for antibodies to cardiac myosin by ELISA as described elsewhere (Kaufman et al. (1993) Nature 366:69–72).

T cell cytotoxic assays: Spleen cells are obtained at different time points after transplantation, and used in antigen-induced T cell cytotoxic assay. Alloreactive cytotoxic T cells are tested for their ability to kill target cells bearing recipient MHC class I molecules associated with donor MHC peptides or CM peptides. As a control, non-immunized mice are used, as well as target cells incubated with either an irrelevant peptide from non-MHC origin (ovalbumin peptide), from self origin or from a third party, non-relevant MHC origin. $2 \times 10^6$ target cells at a concentration of $10^7$ cells/ml in serum-free DMEM are labeled with 100 μCi $Na^{51}CrO4$ (New England Nuclear, Boston, NEN). The targets are then washed and resuspended in medium at $4 \times 10^5$ cells/ml. 50 μl of targets ($2 \times 10^4$) are added to each microwell in triplicate. Spontaneous and total release sample are prepared by adding the targets to wells containing only DMEM or 0.2% SDS, respectively. The plates are centrifuged at 100 g for 5 min and incubated at 37° C. for 5 h. 25 μl of supernatant is collected, deposited onto a glass filter mat, and counted in a Betaplate Liquid Scintillation Counter. Percent specific $^{51}Cr$ release is calculated as follows: 100× (release by CTL−spontaneous release)/(total release−spontaneous release).

What is claimed is:

1. A method of diagnosing the presence of graft rejection against a heart transplanted into a mammalian recipient, the method comprising:

detecting the presence of immune reactivity to autologous contractile proteins expressed in cardiac tissue and native to said mammalian recipient wherein said autologous contractile protein is α-myosin heavy chain;

wherein the presence of said immune reactivity is indicative of rejection of said transplanted heart.

2. The method of claim 1, wherein said immune reactivity comprises the presence of circulating anti-cardiac α-myosin heavy chain antibodies.

3. The method according to claim 1, wherein said graft rejection is chronic graft rejection.

4. A method of diagnosing the presence of graft rejection against a heart transplanted into a mammalian recipient, the method comprising:

detecting the presence of cardiac myosin specific T cells reactive to autologous contractile proteins expressed in cardiac tissue and native to said mammalian recipient;

wherein the presence of said cardiac myosin specific T cells reactive to autologous contractile proteins is indicative of rejection of said transplanted heart.

5. The method according to claim 4, wherein said reactive T cells are TH1 type helper T cells.

6. The method according to claim 5, wherein said detecting step comprises determining the proliferation of a patient lymphocyte sample against an antigen comprising α-myosin heavy chain peptides.

7. The method according to claim 6, wherein said detecting step further comprises determining the cytokine expression of said patient lymphocyte sample in response to said α-myosin heavy chain peptides.

8. The method according to claim 6, wherein said detecting step further comprises performing an ELISA spot assay for the presence of cytokines indicative of TH1 T helper cells.

9. The method according to claim 8, wherein said cytokines are selected from the group consisting of IL-2 and γ-interferon.

10. The method according to claim 4, wherein said reactive T cells are cytotoxic T cells.

11. The method according to claim 10, wherein said detecting step comprises determining the cytotoxicity of a patient lymphocyte sample against labeled cells comprising α-myosin heavy chain peptides.

12. The method according to claim 4, wherein said detecting step further comprises determining the T cell receptor variable region repertoire of a patient lymphocyte sample reactive with α-myosin heavy chain peptides.

* * * * *

UNITED STATES PATENT AND TRADEMARK OFFICE
CERTIFICATE OF CORRECTION

PATENT NO.    : 6,358,751 B1
DATED         : March 19, 2002
INVENTOR(S)   : Benichou, Gilles et al.

It is certified that error appears in the above-identified patent and that said Letters Patent is hereby corrected as shown below:

<u>Column 1,</u>
Line 19, please insert a second paragraph which reads:

-- This invention was made with Government support under Grant No. AI33704, awarded by the National Institutes of Health. The Government has certain rights in this invention. --

Signed and Sealed this

Third Day of December, 2002

JAMES E. ROGAN
*Director of the United States Patent and Trademark Office*